United States Patent

See et al.

[11] Patent Number: 5,870,185
[45] Date of Patent: Feb. 9, 1999

[54] APPARATUS AND METHOD FOR FLUID ANALYSIS

[75] Inventors: Harold J. See; Kenneth D. Turner, both of Abilene; David B. Smith, Merkel; Dan L. Cooper, Abilene, all of Tex.; Gary L. Workman, Madison, Ala.; David B. Purves; G. Wayne Thompson, both of Huntsville, Ala.; Robert A. Mattes, Fayetteville, Tenn.; Darell E. Engelhaupt, Madison, Ala.

[73] Assignees: C.F.C. Technology, Inc., Abilene, Tex.; Univ. of Alabama at Huntsville, Huntsville, Ala.

[21] Appl. No.: 734,231

[22] Filed: Oct. 21, 1996

[51] Int. Cl.$^6$ ..................... G01N 21/41
[52] U.S. Cl. ..................... 356/128
[58] Field of Search ..................... 306/128, 129, 306/133–134, 136, 130, 131, 132, 246, 135, 137–138, 139, 70

[56] References Cited

U.S. PATENT DOCUMENTS

| | | |
|---|---|---|
| H572 | 2/1989 | Hansen . |
| 3,883,233 | 5/1975 | Gulino . |
| 3,895,233 | 7/1975 | Boll et al. . |
| 3,898,558 | 8/1975 | Thompson, Jr. . |
| 3,932,754 | 1/1976 | Riedl et al. . |
| 3,951,607 | 4/1976 | Fraser . |
| 3,976,883 | 8/1976 | Krakow . |
| 3,999,856 | 12/1976 | Unterleitner . |
| 4,013,260 | 3/1977 | McClatchie et al. . |
| 4,027,237 | 5/1977 | Heile . |
| 4,078,896 | 3/1978 | Moen et al. . |
| 4,126,393 | 11/1978 | Sumikama et al. . |
| 4,180,734 | 12/1979 | Gedeon . |
| 4,188,116 | 2/1980 | Bartfay-Szabo . |
| 4,227,806 | 10/1980 | Watkins . |
| 4,229,105 | 10/1980 | Silverbage . |
| 4,232,223 | 11/1980 | Ohnishi et al. . |
| 4,232,224 | 11/1980 | Graham et al. . |
| 4,233,513 | 11/1980 | Elder et al. . |
| 4,236,076 | 11/1980 | Judge et al. . |
| 4,243,321 | 1/1981 | Okuda et al. . |
| 4,256,964 | 3/1981 | Ishida et al. . |
| 4,266,131 | 5/1981 | Ahjopalo et al. . |
| 4,266,862 | 5/1981 | Trotscher et al. . |
| 4,268,479 | 5/1981 | Webster . |
| 4,280,183 | 7/1981 | Santi . |
| 4,286,873 | 9/1981 | Carson . |
| 4,293,198 | 10/1981 | Kohayakawa et al. . |
| 4,304,468 | 12/1981 | Wada . |
| 4,325,635 | 4/1982 | Sattler et al. . |
| 4,327,585 | 5/1982 | Froome . |
| 4,364,271 | 12/1982 | Froome . |
| 4,381,895 | 5/1983 | Hughes et al. . |
| 4,402,820 | 9/1983 | Sano et al. . |
| 4,402,821 | 9/1983 | Yan . |
| 4,451,147 | 5/1984 | Dobes et al. . |
| 4,469,441 | 9/1984 | Bernier et al. . |
| 4,487,503 | 12/1984 | Grandjacques et al. . |
| 4,564,292 | 1/1986 | Omet . |
| 4,571,075 | 2/1986 | Kamrat . |
| 4,591,247 | 5/1986 | Kamiya et al. . |
| 4,593,197 | 6/1986 | Miyatake et al. . |
| 4,640,615 | 2/1987 | Sasaki . |
| 4,641,965 | 2/1987 | Harmer . |
| 4,682,889 | 7/1987 | Harmer . |
| 4,692,024 | 9/1987 | Bloss . |
| 4,761,070 | 8/1988 | Fukuma . |
| 4,806,013 | 2/1989 | Bodenheimer et al. . |
| 4,808,825 | 2/1989 | Miyatake et al. . |
| 4,848,896 | 7/1989 | Matsumoto . |
| 4,877,583 | 10/1989 | Miwa et al. . |
| 4,890,916 | 1/1990 | Rainer . |
| 4,934,818 | 6/1990 | Glantschnig et al. ............ 356/128 |
| 4,952,055 | 8/1990 | Wyatt . |

(List continued on next page.)

*Primary Examiner*—K. Hantis
*Attorney, Agent, or Firm*—Daniel V. Thompson

[57] ABSTRACT

A method and apparatus for fluid analysis includes a sensor for determining the index of refraction of a fluid. Advanced methods of fluid analysis relate index of refraction and other measured physical characteristics of the fluid.

4 Claims, 13 Drawing Sheets

U.S. PATENT DOCUMENTS

| | | |
|---|---|---|
| 4,958,075 | 9/1990 | Mace et al. . |
| 4,981,338 | 1/1991 | Bobb et al. . |
| 4,988,863 | 1/1991 | Bobb et al. . |
| 5,013,920 | 5/1991 | Asano et al. . |
| 5,029,583 | 7/1991 | Meserol et al. . |
| 5,046,018 | 9/1991 | Flewelling et al. . |
| 5,055,688 | 10/1991 | Fabinski . |
| 5,060,505 | 10/1991 | Tury et al. . |
| 5,077,469 | 12/1991 | Fabinski et al. . |
| 5,130,544 | 7/1992 | Nilsson . |
| 5,157,452 | 10/1992 | Suzuki et al. ............................ 356/128 |
| 5,157,454 | 10/1992 | Oka et al. . |
| 5,173,747 | 12/1992 | Boiarski et al. . |
| 5,174,124 | 12/1992 | Paige et al. . |
| 5,184,015 | 2/1993 | Allman et al. . |
| 5,186,899 | 2/1993 | Drago et al. . |
| 5,214,931 | 6/1993 | Paige . |
| 5,218,426 | 6/1993 | Hall et al. . |
| 5,231,591 | 7/1993 | Flewelling et al. . |
| 5,255,527 | 10/1993 | Paige . |
| 5,305,071 | 4/1994 | Wyatt . |
| 5,311,274 | 5/1994 | Cole, Jr. . |
| 5,313,271 | 5/1994 | Chaney . |
| 5,331,409 | 7/1994 | Thurtell et al. . |
| 5,347,358 | 9/1994 | Nebe et al. . |
| 5,355,211 | 10/1994 | Thompson et al. . |
| 5,357,113 | 10/1994 | Liston et al. . |
| 5,362,967 | 11/1994 | Aoki et al. . |
| 5,377,008 | 12/1994 | Ridgeway et al. . |
| 5,392,120 | 2/1995 | Kamiya . |
| 5,394,240 | 2/1995 | Matsumoto . |
| 5,394,244 | 2/1995 | Tsai ........................................ 356/130 |
| 5,410,887 | 5/1995 | Urata . |
| 5,414,506 | 5/1995 | Saisho et al. . |
| 5,419,177 | 5/1995 | Pastorello . |
| 5,422,714 | 6/1995 | Fladd . |
| 5,455,645 | 10/1995 | Berger et al. . |
| 5,455,883 | 10/1995 | Shigeta et al. . |
| 5,493,869 | 2/1996 | Shirley et al. . |
| 5,514,595 | 5/1996 | Olds et al. . |
| 5,524,477 | 6/1996 | Wajid . |

EQUATIONS FOR PRESSURE AND INDEX $$pressure = a + bF + cF^2 + dF^3 + eF^4$$

| FREON | a | b | c | d | e |
|---|---|---|---|---|---|
| R-11 | 2.58096 | 0.06955 | 0.00087 | 4.06E-06 | 1.29E-08 |
| R-12 | 23.9847 | 0.46507 | 0.006515 | -2.42E-07 | 2.04E-07 |
| R-22 | 38.7292 | 0.81165 | 0.00659 | 2.2641E-05 | 2.19E-08 |
| R-113 | 0.85955 | 0.027411 | 3.63E-04 | 2.23E-06 | 1.03E-08 |
| R-114 | 5.953055 | 0.15121 | 1.63E-03 | 7.64E-06 | 1.09E-08 |
| R-123 | 2.02566 | 0.05757 | 7.16E-04 | 4.68E-06 | 1.16E-08 |
| R-134a | 21.3475 | 0.46707 | 5.67E-03 | 8.02E-06 | 6.17E-08 |
| R-500 | 13.297 | 0.5903 | 4.94E-03 | 1.81E-05 | 1.28E-08 |
| R-502 | 31.1128 | 0.91658 | 7.11E-03 | 2.06E-05 | 1.70E-08 |

$$index = k - lF$$

| k | l |
|---|---|
| 1.402 | 0.00037 |
| 1.3183 | 0.00043 |
| 1.2901 | 0.00043 |
| 1.3781 | 0.00028 |
| 1.3207 | 0.00035 |
| 1.3573 | 0.00034 |
| 1.2172 | 0.00033 |
| 1.3048 | 0.00045 |
| 1.2796 | 0.00049 |

FIG. 13

APPARATUS AND METHOD FOR FLUID ANALYSIS

TECHNICAL FIELD

The present invention relates to measuring instruments, and more particularly to devices for analyzing fluids using measurements of index of refraction and other physical characteristics.

BACKGROUND OF THE INVENTION

Refrigerant gases containing chlorine, for example difluorodichloromethane (known as "R12"), have been phased out of use in new refrigeration systems for their harmful effects on the environment. Tight regulatory controls have been imposed governing the reuse and reclamation of such refrigerants.

As a result of the new regulatory standards, it has become common to find refrigerant systems that are contaminated by additions of other more readily-available refrigerants. A common "shade-tree" mechanic technique for repairing an automotive refrigeration system is to add R134a or R2 to an R12 system. R134a is now a commonly available non-chlorinated refrigerant, whereas R12 and R22 are not available. Many cars in the southern and western parts of the United States now contain unoriginal mixtures like two-thirds R12 and one-third R22. Similarly, in the past, it was known that an old refrigerator could be "juiced" to make it work a little while longer. The result in either case is an adulterated mixture of refrigerants, which plays havoc with the current requirements for reclaiming and recycling all chlorinated refrigerants. Currently, regulations permit contamination of only 0.5% in reusable, reclaimed refrigerant.

Thus, there presently exists a need for an instrument that HVAC and MVAC technicians can use to analyze refrigerants for identity of refrigerants and their purity.

One prior attempted solution to the problem is disclosed in U.S. Pat. No. 5,498,873. That solution, based on infrared absorption, was incomplete in a number of respects. The technique is similar to Near Infra-red Spectroscopic (NIR) techniques that have been used on contamination detection on critical space hardware. In practice, all species of refrigerant containing a hydrogen, such as the HCFC's, are easily distinguishable. The major difficulty is that if the two refrigerants were different in Cl or F, but contained the same number of H's on each carbon, then the NIR spectra are not easily distinguishable. The refrigerants R20, TCA, and TCE, each containing one or more hydrogens, are easily distinguishable. In contrast, both R113 and R11 contain no hydrogens and show no spectra in the NIR. Further, TCA and R141b, each containing three hydrogens on one carbon, are very nearly indistinguishable in the NIR. Thus there are significant drawbacks in using NIR for identification of a specific refrigerant.

In contrast, it has been found that the indices of refraction of the refrigerants in the liquid state may be readily used to separate out the species by that property. Index of refraction is defined as the angular change in a beam of light passing through the interface of two different substances. The technique of using index of refraction is based on the fact that each refrigerant has a different atomic composition and therefore a different index of refraction. Since the index of refraction is linear with respect to any two components, fairly accurate estimates of two component mixtures can be made.

A difficulty arises, however, in obtaining a reliable measurement of the more volatile refrigerants and comparing that to known values. Good control of temperature and pressure are required. Commercial index of refraction measuring instruments, such as the Abbe refractometer, already exist for liquids; but there are no instruments available which are capable of handling volatile species, such as R12, R22, etc. Hence, an instrument which can be used to perform index of refraction measurements on the volatile refrigerants in standard containers and refrigerating systems is required.

Thus a need presently exists for an instrument which can measure the index of refraction of all the comnmonly-available refrigerants and can be mounted on any standard connection to an AC system or bottle. The instrument must be temperature controlled to establish the index measurement for each specific refrigerant. These temperatures will be established beforehand, making the measurement very straight-forward for the technician making the measurement.

The two refrigerants closest in index of refraction are R12 and R123, which have indices of 1.2870 and 1.2754, respectively. Thus, measuring index of refraction to 4 significant figures will be a necessity.

A refrigerant monitor must be small and rugged enough for a technician to carry the unit to the equipment requiring a sample to be analyzed to determine which refrigerant and to what purity level was currently contained in the equipment.

SUMMARY OF THE INVENTION

The present invention in its simplest aspect provides a simple and rugged instrument for measuring the index of refraction of a fluid. A sample of the fluid is introduced into a sample chamber, and a source of light is passed through the interface of the fluid and a window in the chamber. An angle detector is positioned outside the chamber and adapted to determine the angle of the light emerging through the window, which leads to a direct determination of the index of refraction.

In a more specific aspect of the invention, the index of refraction measurement is combined with at least one other measured physical characteristic of the fluid sample, such as temperature or pressure, and then the fluid is identified by reference to known, pre-determined relationship data for a plurality of different fluids. In a more advanced apparatus, both temperature and pressure are measured and combined with the index of refraction measurement, and then the temperature is varied to obtain additional data, to identify the constituents of two-part ("binary") mixtures of certain fluids and measure the percentages of the mixtures.

In one embodiment, this invention was used in a device known as the Refrigerant Monitoring System ("RMS") providing instrumentation and software for monitoring the purity of CFC's, HCFC's and other refrigerants. This embodiment provides identification and purity of a specific CFC or HCFC refrigerant based upon the measurement of its index of refraction and/or hydrostatic pressure at measured temperatures. Binary mixtures, and to some degree higher order mixtures, can be analyzed using index of refraction and hydrostatic pressure measurements taken at several temperatures. The simple quality monitoring of refrigerants in specific classes of HVAC units (including automotive) or refrigerant recovery systems can be accomplished using index of refraction measurements alone. Extending the scope to include the identification of refrigerants and binary mixtures in a broad class of refrigerants requires the use of both index of refraction and hydrostatic pressure.

BRIEF DESCRIPTION OF THE DRAWINGS

A more complete understanding of the invention and its advantages will be apparent from a review of the Detailed Description in conjunction with the following Drawings, in which.

DETAILED DESCRIPTION OF THE PREFERRED EMBODIMENT

In one specific form, the invention is incorporated in a specific device developed to monitor refrigerants. While the Refrigerant Monitoring System ("RMS") is described in detail herein, applications of the invention are not limited to refrigerant analysis, and many other environments will be found for beneficial use of the invention. For example, the device in its simplest form is a small, inexpensive, and rugged refractometer for making primary measurements of indices of refraction. The principles of fluid analysis invented in connection with the RMS can be used by those skilled in the art for analyzing fluids of any character, such as contaminated surface water, blood, beverages, etc.

The RMS described in detail herein is a portable instrument which provides an identification of the Freon®-type refrigerants used in HVAC and MVAC systems in situ and a purity indication, utilizing the measurement of index of refraction in the liquid state at measured temperatures and/or combined index of refraction measurement with vapor pressure of the liquid. The RMS provides an indication when the soluble impurities in the refrigerant exceed a given threshold, which preferably is 0.5% according to current regulatory requirements.

The system includes a thermistor to measure fluid temperature, a refractometer capable measuring absolute indices of refraction from 1.1500 to 1.4000, with a resolution of 0.0002 (±0.0001), and a pressure sensor to measure the pressure of the fluid. The primary measurement of index of refraction is used to provide an initial estimate of refrigerant identification and quantification, with the hydrostatic pressure measurement used to provide a secondary discrimination between refrigerant components with similar indices of refraction and to analyze mixtures.

Figure 11:
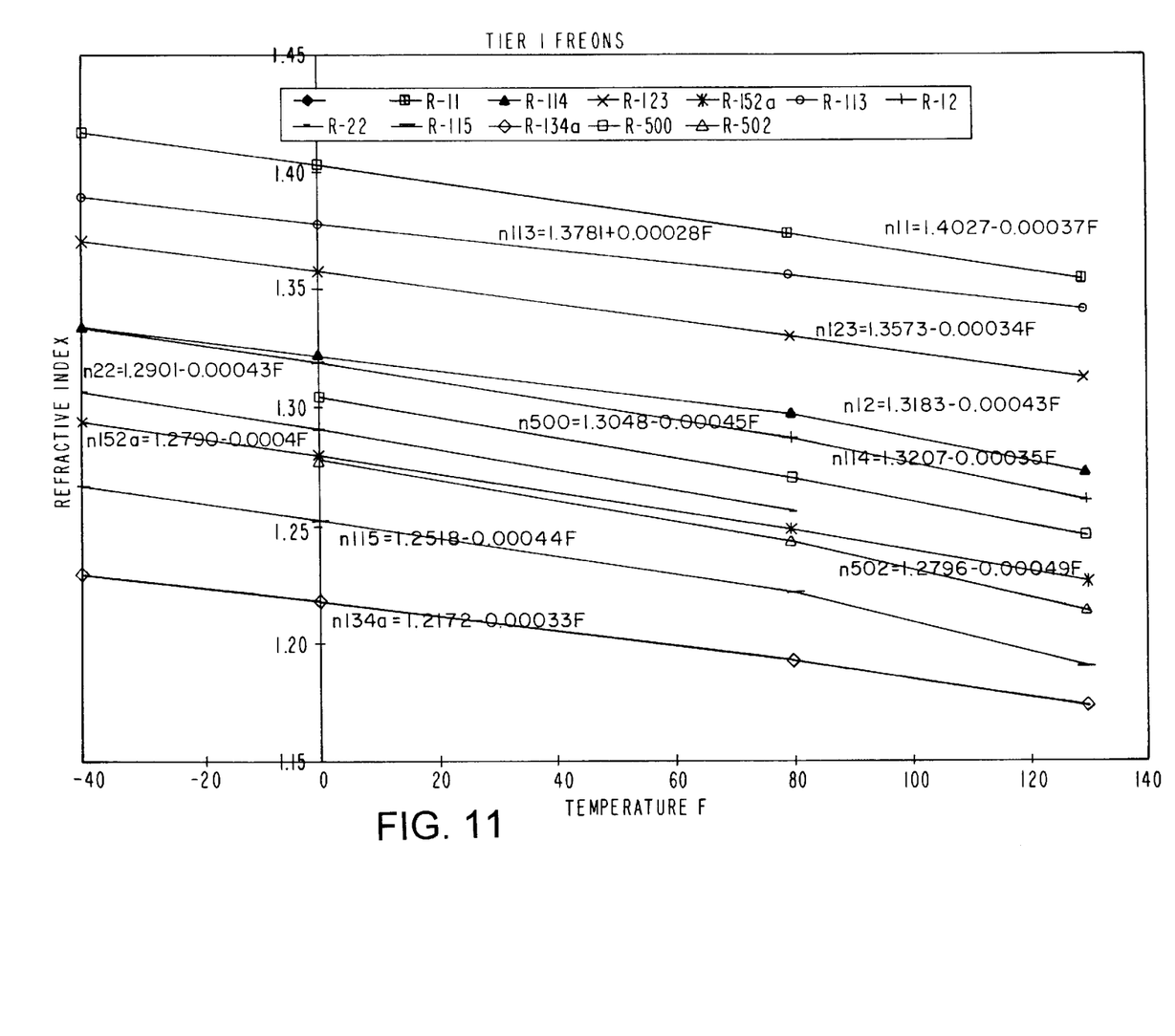
FIG. 11 shows the relationship of index of refraction of refrigerants with respect to temperature.
Figure 12:
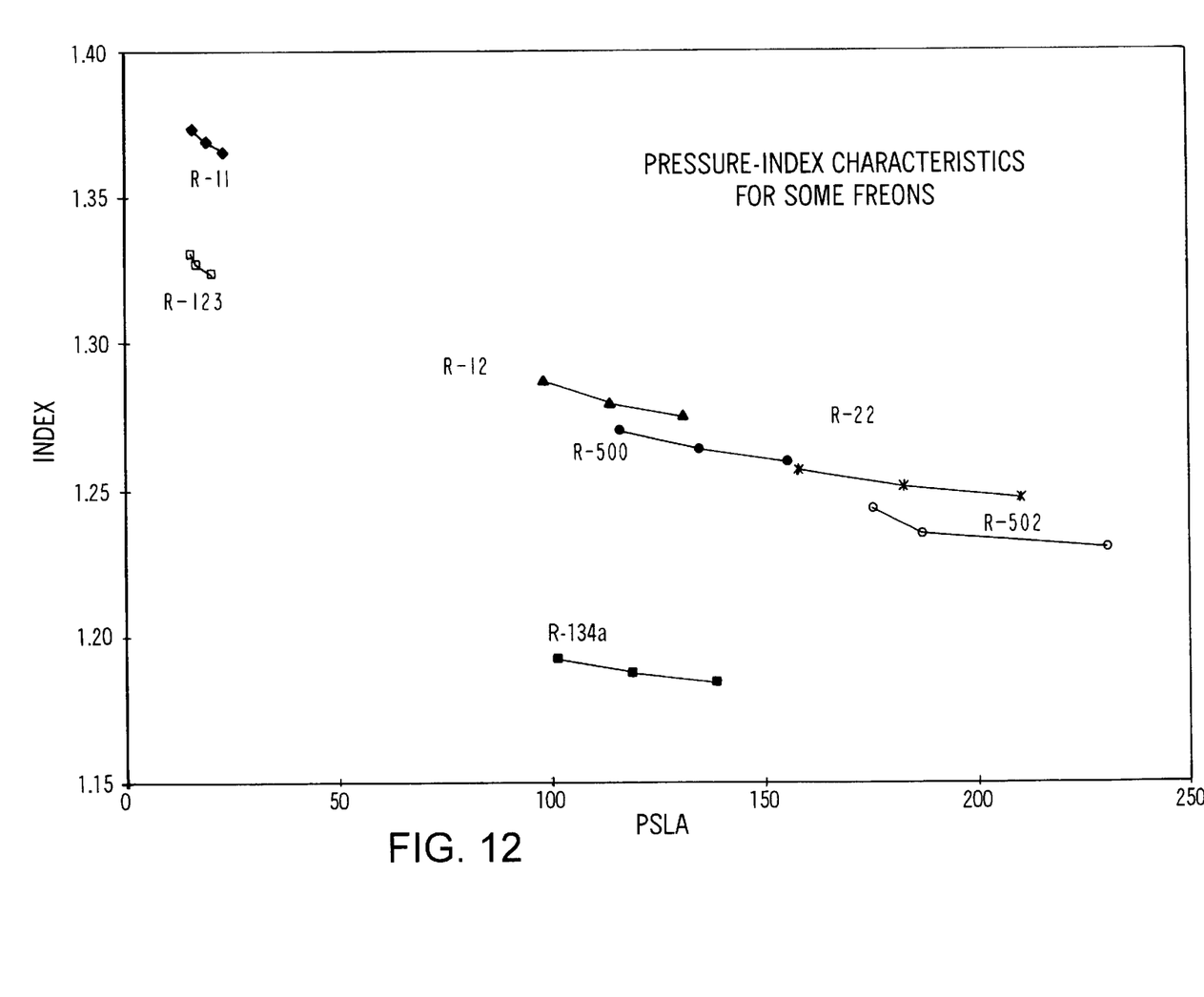
FIG. 12 shows the vapor pressure relationship to index of refraction at various temperatures and FIG. 13 shows a listing of the mathematical formulae relating index of refraction, temperature and pressure.
Figure 13:
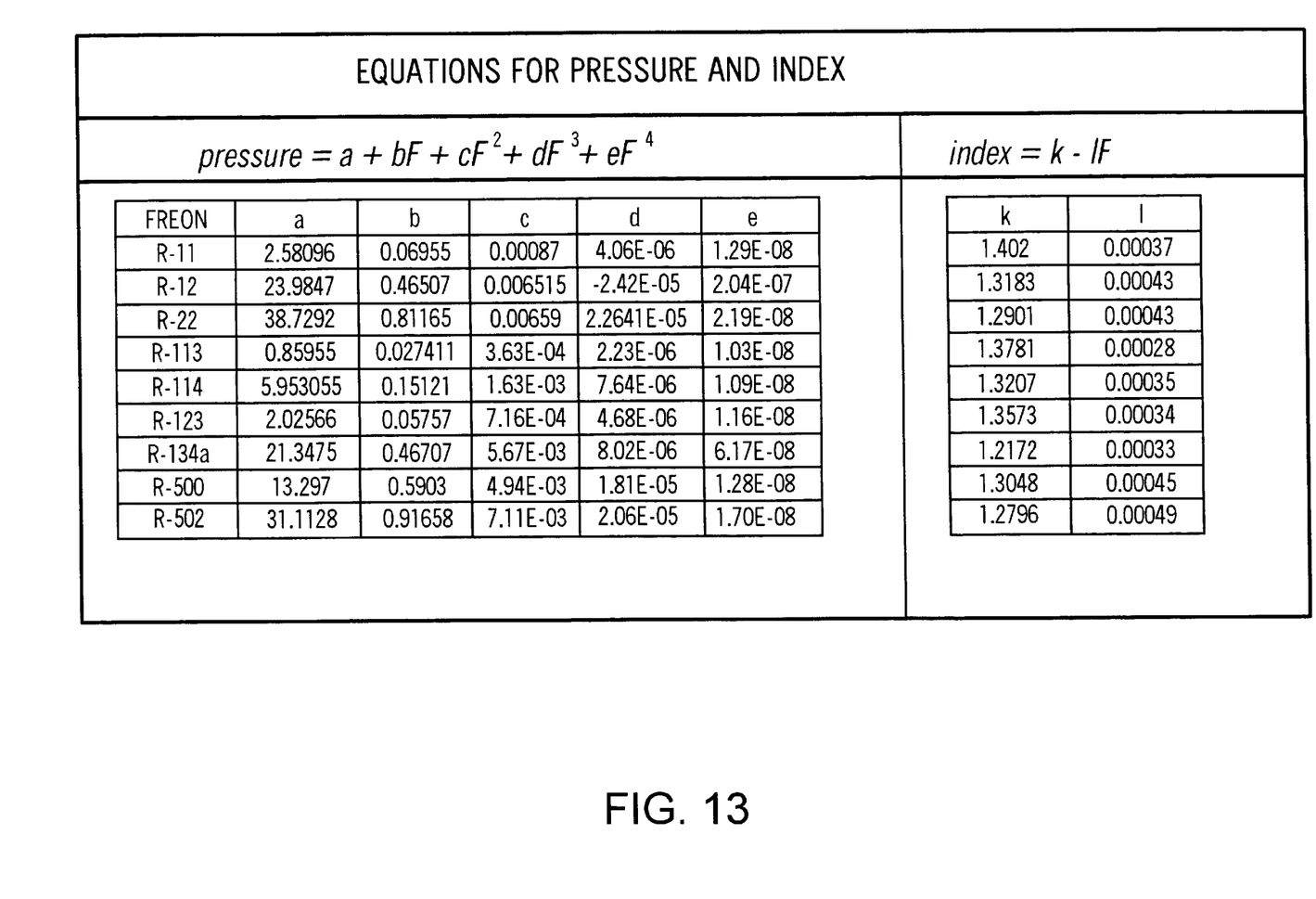

The relationship of index of refraction of refrigerants with respect to temperature is known from published references and shown in FIG. 11. FIG. 11 also includes the mathematical formulae for the index/temperature relationships, expressed in the form $n\#\#\# = C_1 - C_2 * F$, where $C_1$ and $C_2$ are constants, F is temperature and $n\#\#\#$ is the index of refraction for a given refrigerant ###. Most of the pure refrigerants can be identified easily by measuring and correlating the index of refraction and temperature of a sample. To expand the coverage to include binary mixtures and separate out the species with close indices of refraction, the ability to make vapor pressure measurement at various temperatures is included. FIG. 12 shows the vapor pressure relationships to index of refraction at various temperatures. FIG. 13 is a listing of the mathematical formulae relating index of refraction, temperature and pressure.

Figure 1:
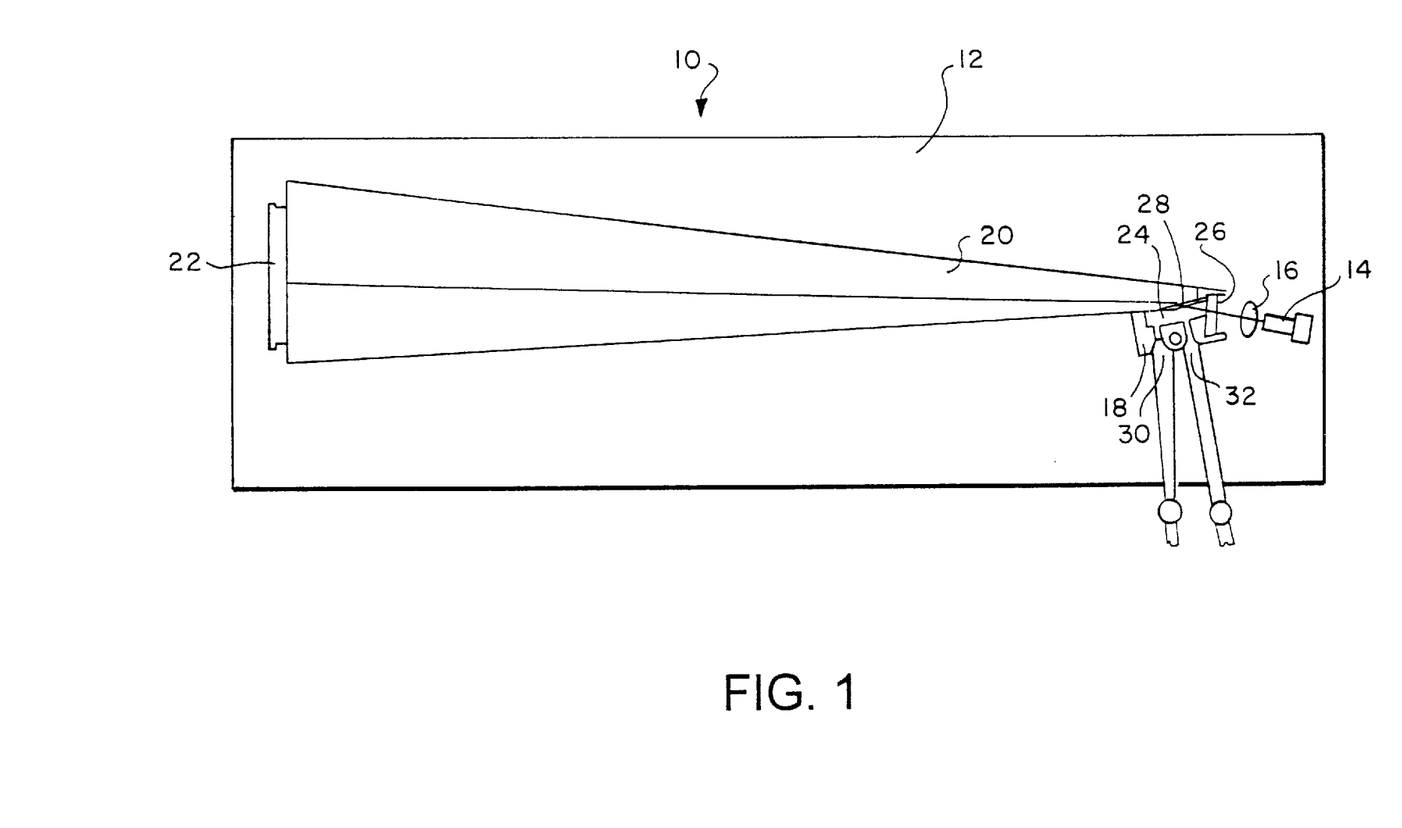
FIG. 1 is a schematic diagram illustrating the basic refractometer section of the invention.
Figure 2:
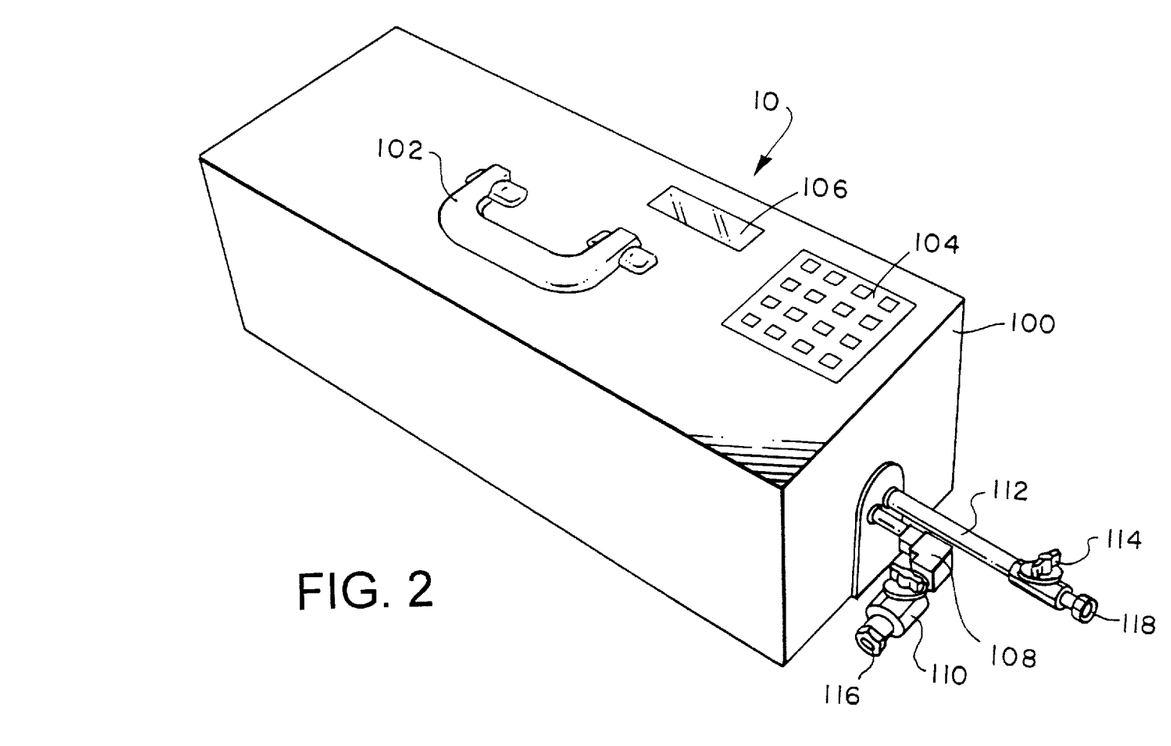
FIG. 2 is perspective view of the invention.

The construction of the refractometer includes a unique design to obtain a continuously diverging angular dependence on index of refraction of the fluid by optically coupling a transparent positioner of higher index of refraction to a transparent sample cell window. Therefore the resolution of the index of refraction measurement can be improved merely by extending the optical path of the instrument. FIG. 1 illustrates the basic concepts of the index of refraction measuring apparatus.

Referring to FIG. 1, the index of the fraction measuring apparatus 10 includes a planar base 12 upon which the various components are mounted. The components include a diode laser 14 at one end of the base 12, a lens 16, a sample cell 18, a positioner 20, and an angle detector 22 at the other end of base 12. Laser 14 is a source of light positioned exterior of sample cell 18 to direct light into the sample chamber 24 through first transparent window 26. Light exits sample chamber 24 and sample cell 18 through second transparent window 28. Light exiting window 28 travels through positioner 20, which preferably is a transparent block of acrylic plastic. Angle detector 22 is preferably an array of photodiodes adapted to determine the angle of light exiting sample cell 18 with respect to the sample cell. Sample cell 18 has walls defining sample chamber 24, as well as an inlet opening 30 and an outlet opening 32 for introducing a fluid sample into the sample chamber 24.

The angle $\sigma_w$ of refracted rays in the positioner are determined by Snell's Law, $\sigma_w = \mathrm{SIN}^{-1}(n_f * \sin \sigma_0 / n_w)$, in the usual manner. The light beam from laser 14 enters cell 24 at 85 degrees with respect to second window 28. All refracted rays begin at the same point of origin due to the fixed relationship of the laser and the sample cell. Optimal dispersion and resolution can be achieved by having the refractive indices of each successive element, including the window and transparent positioner and any optical coupling therebetween, to be always increasing. Intensity distribution over several array elements in angle detector 22 is used to interpolate between elements, thereby increasing overall resolution.

Referring to FIGS. 2–5, where like numerals indicate like and corresponding elements, apparatus 10 includes a cover 100 having a carrying handle 102. Keypad 104 and display 106 are provided on the top face of cover 100. Inlet conduit 108 includes a valve 110, and similarly outlet conduit 112 includes a valve 114. Conduits 108, 112 terminate at connection fittings 116, 118.

Figure 3:
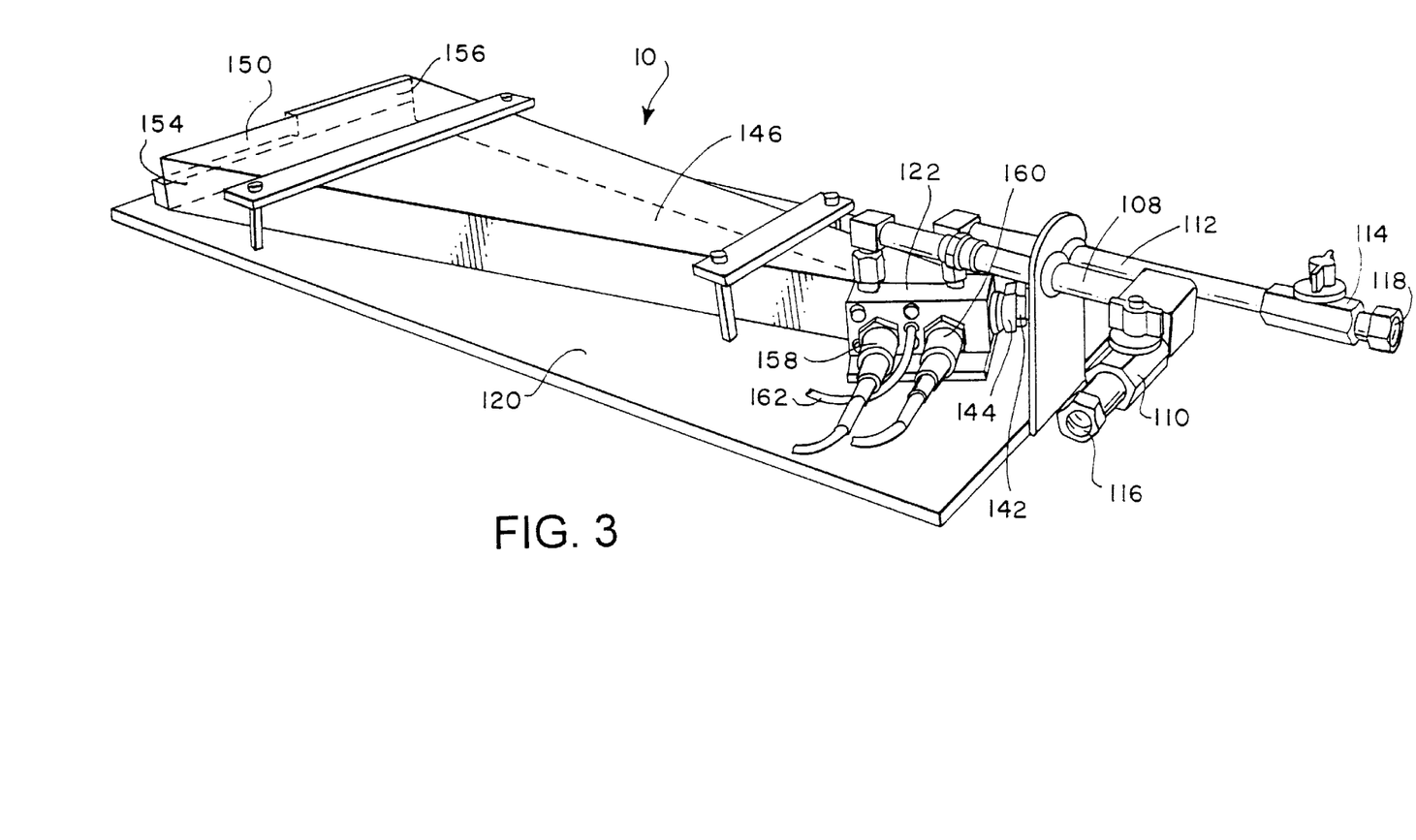
FIG. 3 is a view similar to FIG. 2 with the cover removed.
Figure 4:
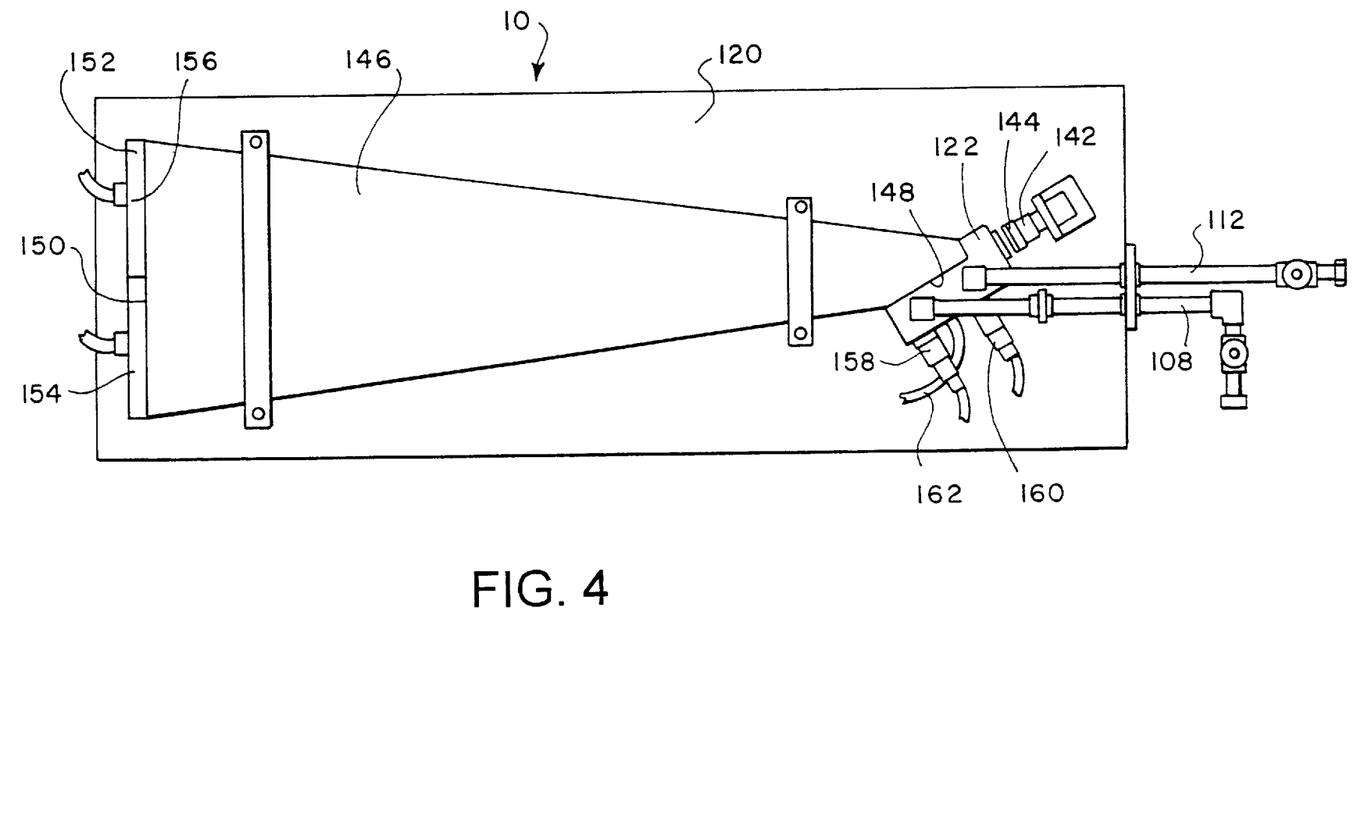
FIG. 4 is a top view of the apparatus of FIG. 3.
Figure 5:
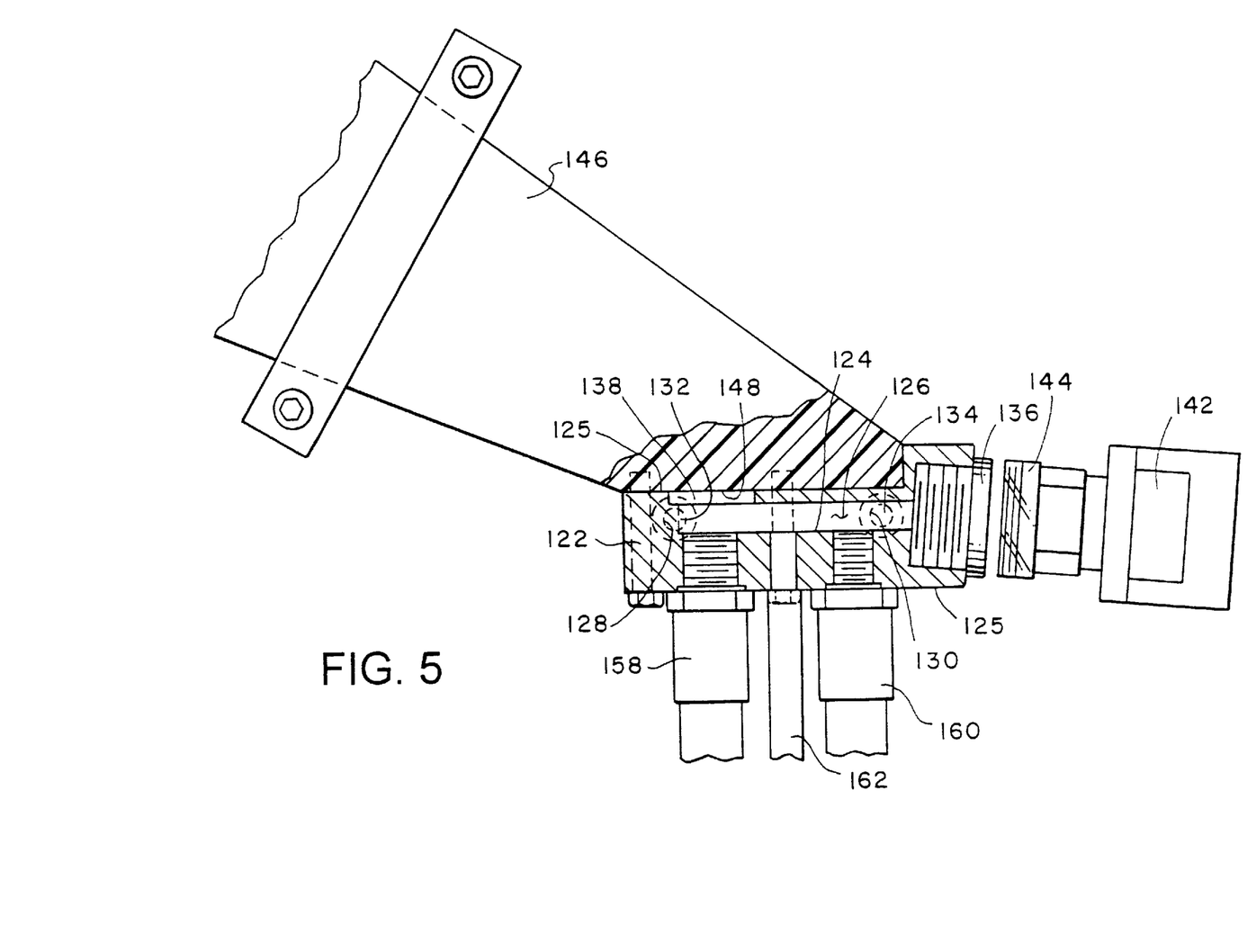
FIG. 5 is an expanded view of the sample cell.

FIGS. 3–5 illustrate apparatus 10 with cover 100 removed. The components of the index of refraction apparatus are fixed to a planar base 120. The components include hollow sample cell 122, having interior and exterior walls 124, 125. The interior walls 124 define a sample chamber 126 (FIG. 5). Sample cell 122 further has walls 128, 130 defining inlet and outlet openings 132, 134 through the interior and exterior walls 124, 125 for introducing a fluid sample into the sample chamber. Sample cell 122 further has first and second opposed, spaced-apart transparent windows 136, 138. A laser 142 is positioned exterior of the sample cell 122 opposite the first window 136. Lens 144 is interposed between the laser 142 and the first window 136 for transforming the light emitted by the laser 142 into a line of light. The laser 142, lens 144, and first and second windows 136, 138 are adapted and arranged such that a line of laser light is directed into the sample cell 122 through the first window 136, through the sample chamber 126, and out of the sample cell 122 through the second window 138.

A transparent positioner 146, or "waveguide", is connected to an exterior wall 125 of sample cell 122 and has a first face 148 opposite the second window 138 and a second face 150 (FIGS. 3 and 4) spaced apart and opposite from the first face 148. In the preferred embodiment, the windows are made of borosilicate, brand name Borofloat by Edmund Scientific. Preferably, a thin film of transparent optical-coupling fluid (not shown) is interposed between first face 148 and second window 138, the fluid having an index of refraction between that of the window and the positioner. Angle detector 152 is connected to the second face 150 of the transparent positioner 146. In preferred form, angle detector 152 includes two linear photodiode arrays 154, 156 staggered as shown in FIGS. 3 and 4. Angle detector 152 is adapted to determine the angle of the line of light exiting the sample cell 122 with respect to the sample cell, with the linear arrays 154, 156 being arranged perpendicular to the line of laser light exiting the second window 138. The arrays 154, 156 are adapted to generate an electrical signal indicative of light-sensitive elements illuminated by the line of laser light. Improved resolution in the measurement of refracted angle is achieved by scanning over the pixel distribution illuminated and calculating the location (even if between pixels) of maximum intensity. The laser 142 is shown spaced apart from the sample cell, but it could be connected to the sample cell by an additional transparent positioner similar to positioner 146.

In the more complex version of the invention designed for fluid analysis, as opposed to simple index of refraction measurement, angle detector 152 is a first sensor for determining the index of refraction of a fluid sample in sample cell 122. A second sensor 158 is provided for determining at least one additional physical characteristic of the fluid sample, and a third sensor 160 determines at least another additional characteristic of the fluid sample. Yet another sensor 162 may be used to determine the electroconductivity of the fluid sample, for determining water contamination.

Figure 6:
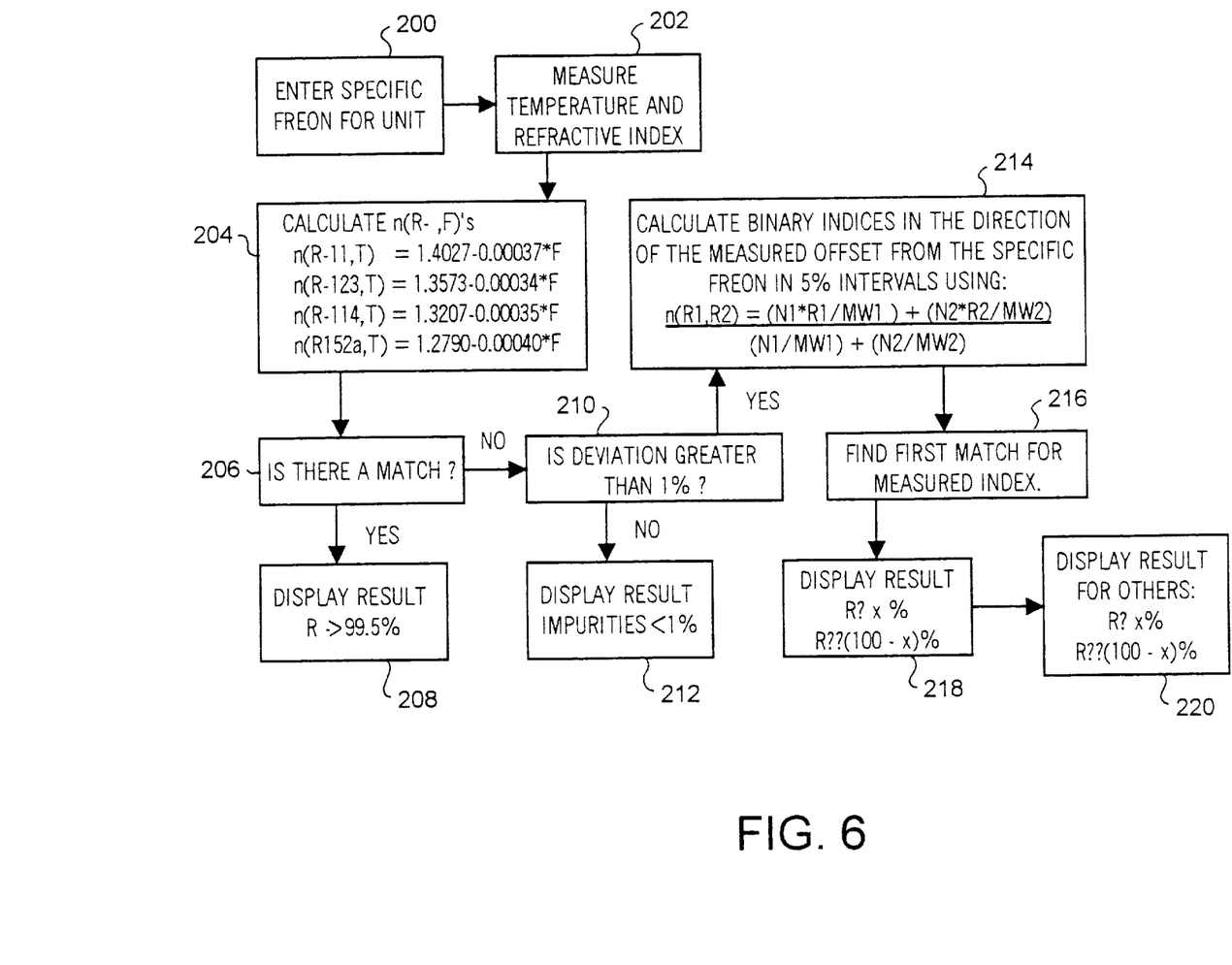
FIGS. 6 and 7 are flow diagrams of the software algorithms used with the invention.
Figure 7:
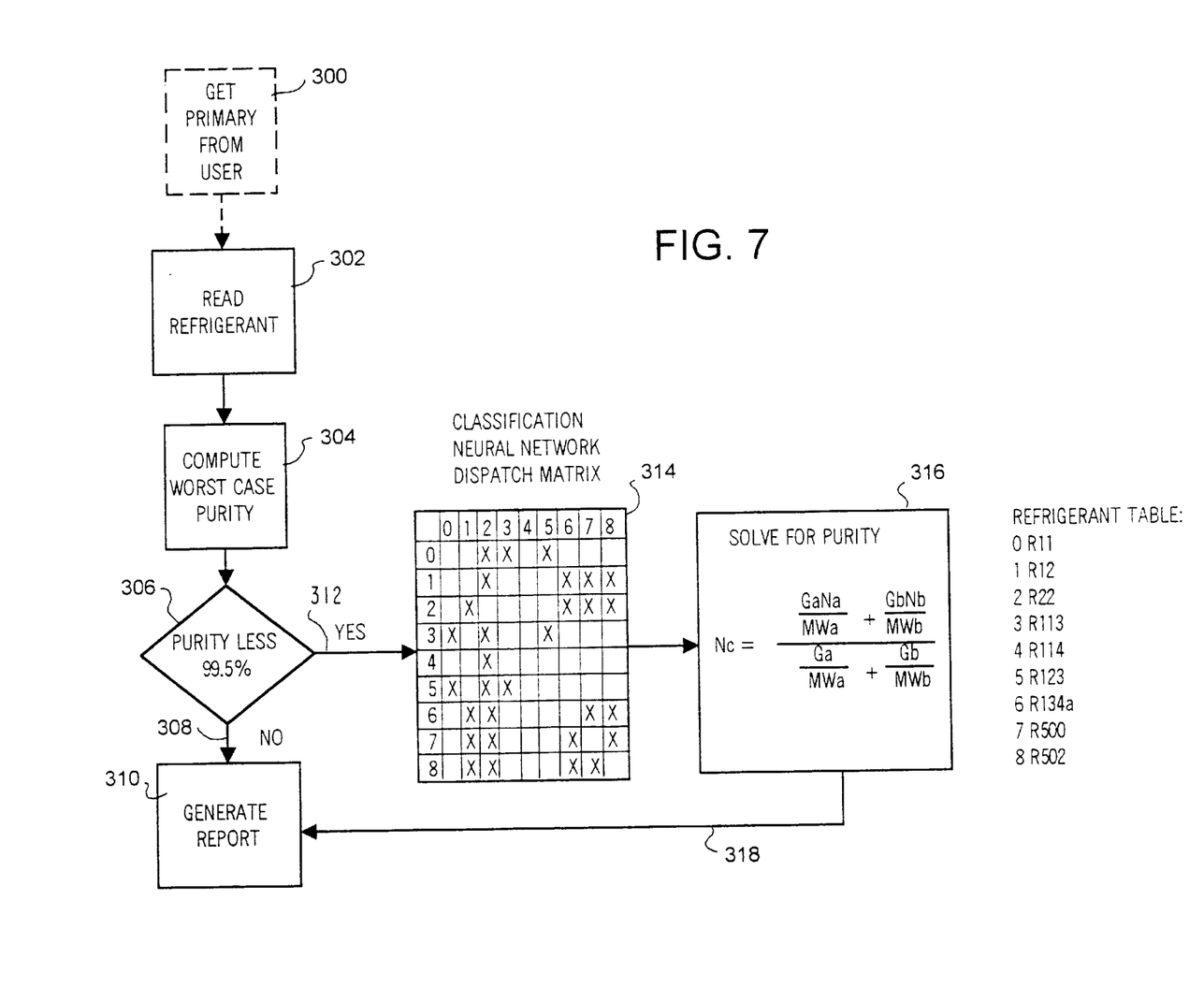

The software algorithms used to determine specific refrigerant purity and composition of binary mixtures are illustrated in FIGS. 6 and 7. Discrimination between binary mixtures and refrigerants with similar characteristics is achieved using multivariate analysis (FIG. 6) or neural networks (FIG. 7).

Referring to FIG. 6, where only index of refraction and temperature are measured, the refrigerant sample is placed in sample cell 18 in step 200. The temperature and index of refraction are measured in step 202. In step 204, index of refraction is related to temperature, and in step 206 a decision is made as to whether there is a match between the related index and temperature with known relationship data. If there is a match, the identity of the refrigerant is displayed at step 208.

If there is not a match, then the deviation is determined at step 210. If the deviation is less than 0.5 percent, then that information is displayed at step 212. If the deviation is greater than 0.5 percent, then calculations are done as shown in step 214 to determine the probable binary mixture of refrigerants. The first match for binary mixtures is determined in step 216, and displayed in steps 218–20.

Better discrimination between mixtures and their components is available where a third physical characteristic such as pressure is used in the analysis algorithm. Pressure can be used to resolve ambiguous or poor matching between mixture components and known relationship data.

FIG. 7 illustrates a software algorithm that utilizes index of refraction, temperature, and pressure and their known relationship data, to solve for purity and mixture component using neural networks. Calibration data is loaded into the apparatus at step 300. Step 302 begins the analysis of any given sample, where the physical characteristics of index of refraction, temperature, and pressure are measured. The identification of a single refrigerant with its associated purity is analyzed at step 306, similar to the steps employed in FIG. 6. If a single refrigerant with a purity of 99.5% or greater is detected, then a report to that effect is generated via branch 308 at step 310. In the event an impure refrigerant mixture is detected via branch 312, then the solutions in step 314 are applied. Step 314, entitled Classification Neural Network Dispatch Matrix, is a vector of nine methods, eight of which are neural nets, each with six inputs and nine outputs. The method to be used is based on a major refrigerant component. Given two sets of data (pressure, temperature, index of refraction), generated by measuring the data at one temperature and then heating or cooling the sample to get the second set of data, the appropriate method classifies the secondary refrigerant component. The data is passed to a function which solves for the percentages of each constituent. The difference between the non-neural network method described in FIG. 6 is that the method of FIG. 6 merely moves on the percentage function, assuming there is only one reasonable refrigerant mixture with any given primary component. In Step 316, the purity is solved, with the variable names indicated as follows:

| | |
|---|---|
| Na | index of refraction of A |
| Nb | index of refraction of B |
| Nc | index of refraction of the mixture of A and B |
| Ga | concentration of A |
| Gb | concentration of B, equal to (1.00-Ga) |
| MWa | molecular weight of A |
| Mwb | molecular weight of B |

A report is then generated via branch 318.

Software code listings have been submitted with this application as an Appendices. Software Appendix 1 applies to FIG. 6, and Software Appendix 2 applies to FIG. 7.

Figure 8:
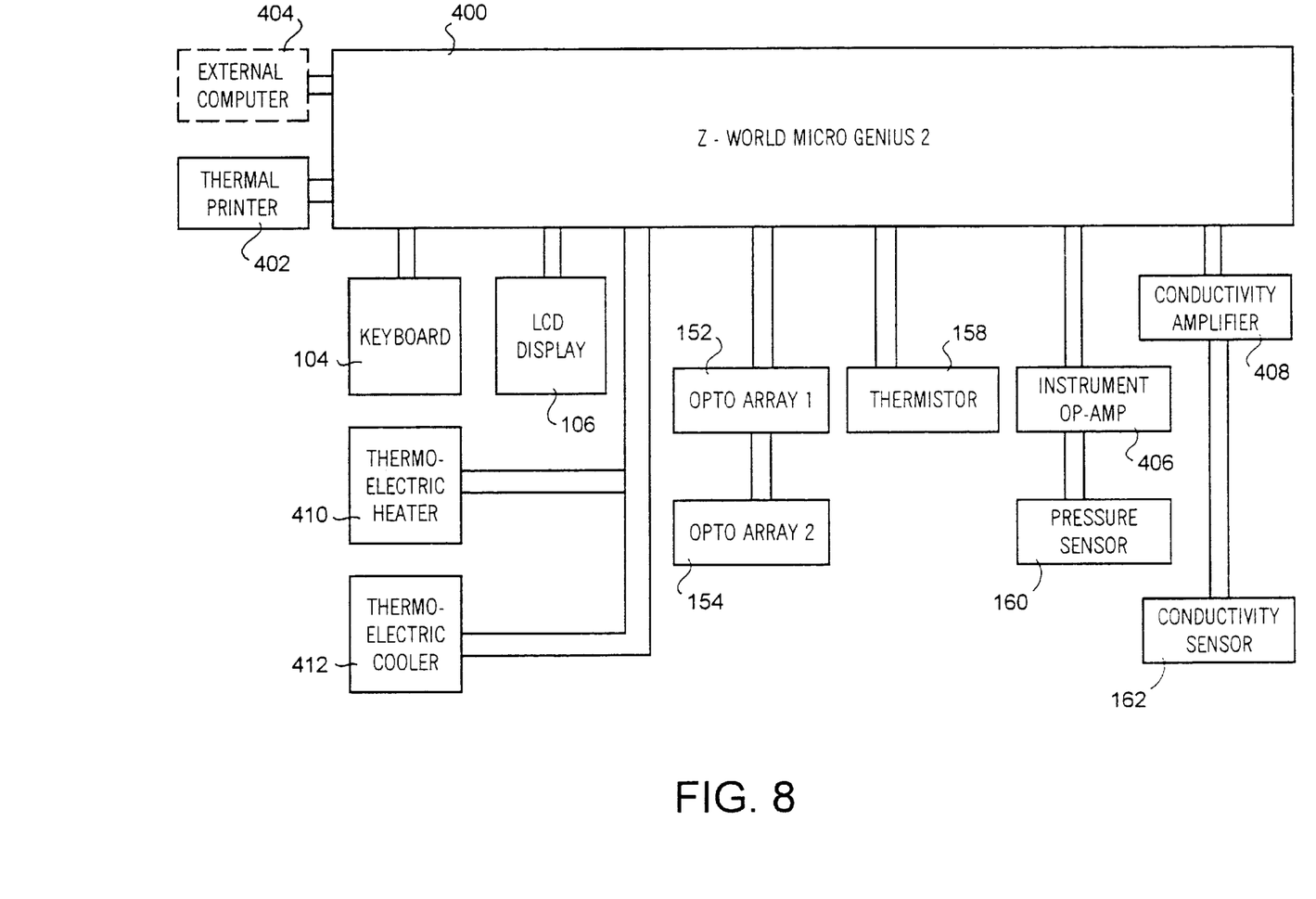
FIGS. 8–10 are diagrams of the electrical hardware used with the invention.
Figure 9:
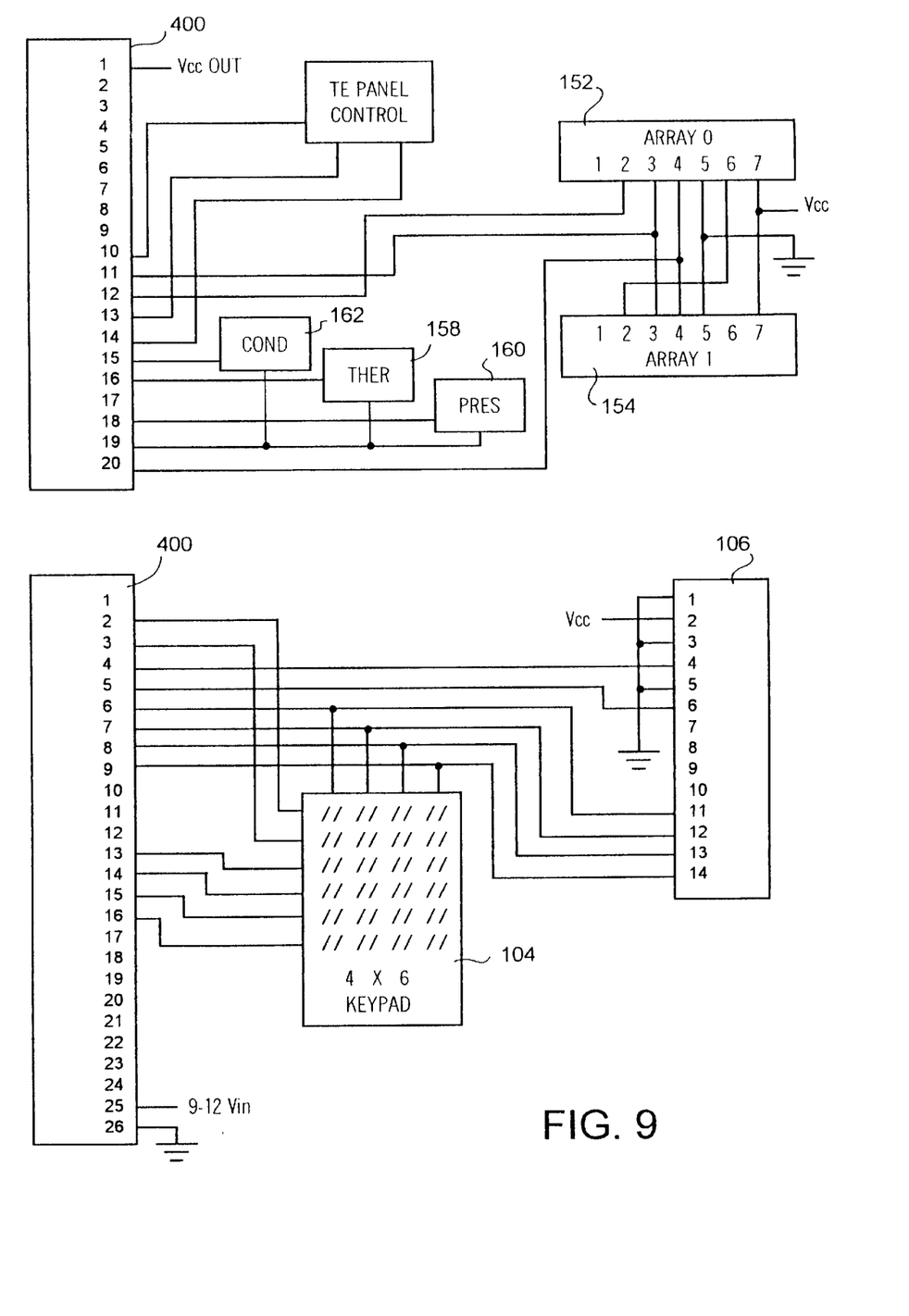
Figure 10:
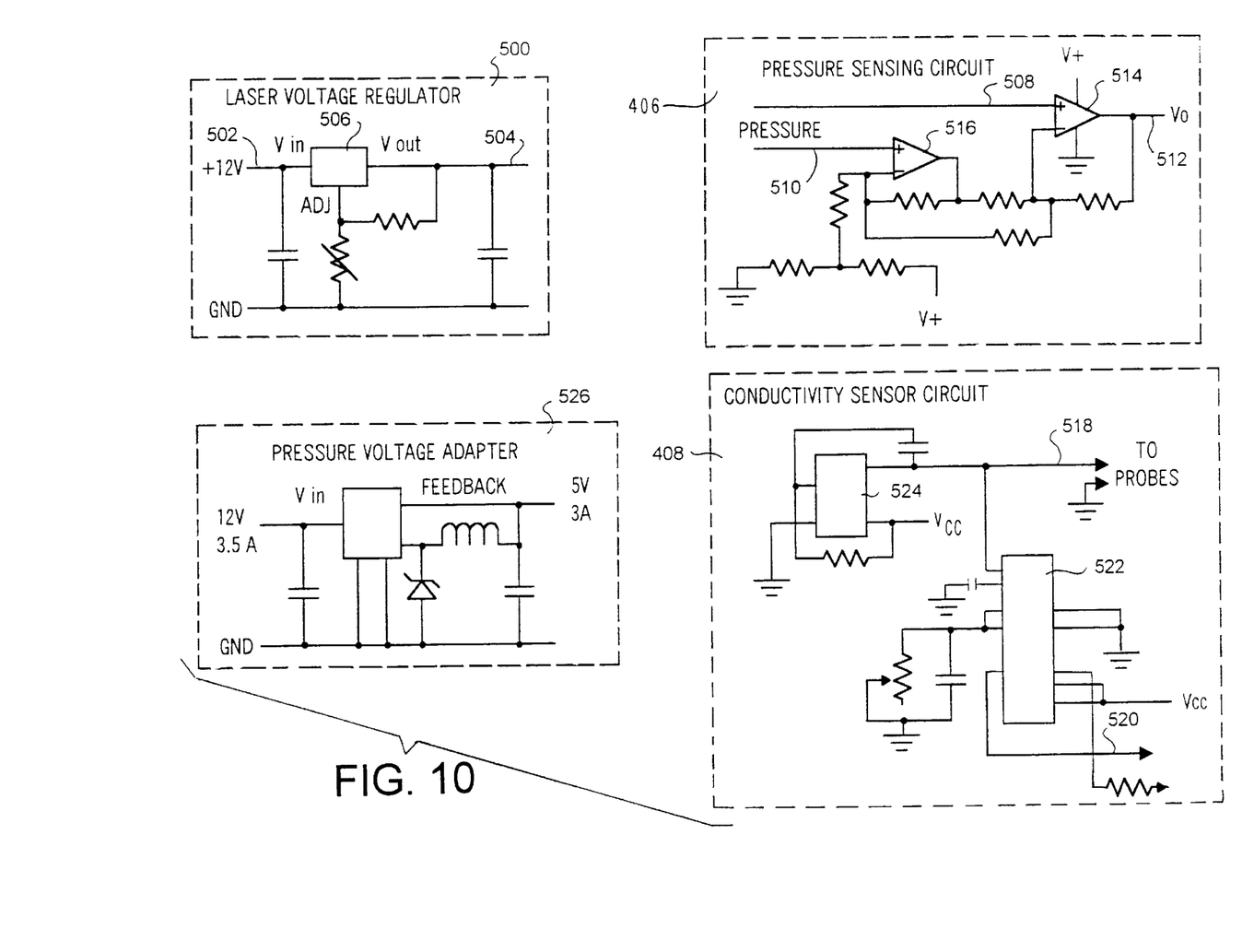

A computer and display hardware used in connection with the algorithms just described is illustrated in FIGS. 8–10. The hardware includes a microprocessor board 400, which in the preferred embodiment is a Micro Genius 2 board manufactured by Z-World Engineering, Inc. Keyboard 104, display 106 and thermal printer 402 are the user input/outputs. A provision is made so that an external computer 404 may be connected for calibration and setup purposes. The photodiode arrays 152 and 154 are connected to the microprocessor board 400. In the preferred embodiment, arrays 152 and 154 are each a model TSL218 array manufactured by Texas Instruments. Temperature sensor 158 in the preferred embodiment is a Radio Shack Model No. 271-110. Pressure sensor 160 in the preferred embodiment is a model 19C500AM made by Sensym, and is connected to microprocessor board 400 by way of an instrument op-amp circuit 406. Conductivity sensor 162 is connected to microprocessor board 400 by way of a conductivity amplifier 408. Circuits 406 and 408 are described below in connection with FIG. 10. Thermo-electric heater 410 and thermo-electric cooler 412 are provided to vary the temperature of the sample to collect additional sets of data, for use with the algorithm of FIG. 7, to more accurately determine the percentages and constituents of binary mixtures.

Referring now to FIG. 9, the pin connections for microprocessor board 400 include the connections to arrays 152, 154 and the sensors 158, 160, and 162. LCD display 106 and keypad 104 are connected as shown.

Referring now to FIG. 10, the support circuits for the apparatus include the laser voltage regulator circuit 500 which drops the twelve volt power supply at 502 to the required voltage for the laser at 504, via integrated circuit 506. In the preferred embodiment, laser 142 is a five mW 670 nm semiconductor diode laser manufactured by Meredith Instruments, although different types and wavelengths of lasers may be employed. In circuit 406, the input from pressure sensor 160 is placed on lines 508, 510, and converted to an output voltage at line 512 by way of op amps 514, 516. In circuit 408, the input from conductivity probe 162 is placed on line 518. The amplified output is sent to the microprocessor board via line 520, after amplification in integrated circuits in 522 and 524. In circuit 526, the voltage for the printer is dropped from 12 to 5 volts.

Whereas, the present invention has been described with the respect to a specific embodiment thereof, it will be understood that various changes and modifications will be suggested to one skilled in the art, and it is intended to encompass such changes and modifications as fall within the scope of the appended claims.

We claim:

1. Apparatus for measuring the index of refraction of a fluid, comprising:

a hollow sample cell having interior and exterior walls, with the interior walls defining a sample chamber;

the sample cell further having walls defining inlet and outlet openings through the interior and exterior walls for introducing a fluid sample into the sample chamber;

the sample cell further having first and second opposed, spaced-apart, transparent windows;

a laser positioned exterior of the sample cell opposite the first window;

the laser and first and second windows positioned with respect to each other such that laser light is directed into the sample cell through the first window, through the sample chamber, and out of the sample cell through the second window;

a transparent positioner connected to an exterior wall of the sample cell and having a first face opposite the second window and a second face spaced apart and opposite from the first face; and an angle detector connected to the second face of the transparent positioner for determining the angle of the light exiting the sample cell with respect to the sample cell, the angle detector including a linear array of light-sensitive elements, the array operable to generate an electrical signal indicative of light-sensitive elements illuminated by the laser light; and a computer for determining the index of refraction from the electrical signal.

2. The apparatus of claim 1 including a display electrically connected to the computer for visually indicating the index of refraction.

3. The apparatus of claim 1 with a transparent optical coupling fluid between the second window and the transparent positioner.

4. The apparatus of claim 3 with the second window, coupling fluid and transparent positioner having ever-increasing indices of refraction with each successive element, such that the resolution of the apparatus is increased with the distance between the sample cell and the positioner.

* * * * *